US00PP34514P2

(12) United States Plant Patent
Slaughter et al.

(10) Patent No.: US PP34,514 P2
(45) Date of Patent: Aug. 23, 2022

(54) NECTARINE TREE NAMED 'WANECTFIVE'

(50) Latin Name: *Prunus persica nucipersica*
Varietal Denomination: 'Wanectfive'

(71) Applicant: Wawona Packing Co., LLC, Cutler, CA (US)

(72) Inventors: John Keith Slaughter, Fresno, CA (US); Kaylan M. Roberts, Fresno, CA (US)

(73) Assignee: Wawona Packing Co., LLC, Cutler, CA (US)

( * ) Notice: Subject to any disclaimer, the term of this patent is extended or adjusted under 35 U.S.C. 154(b) by 0 days.

(21) Appl. No.: 17/300,763

(22) Filed: Oct. 26, 2021

(51) Int. Cl.
*A01H 5/08* (2018.01)
*A01H 6/74* (2018.01)

(52) U.S. Cl.
USPC ..... Plt./188

(58) Field of Classification Search
USPC ..... Plt./187, 188, 189
See application file for complete search history.

(56) References Cited

U.S. PATENT DOCUMENTS

| | | | |
|---|---|---|---|
| PP18,706 | P2 | 4/2008 | Bradford |
| PP26,610 | P3 | 4/2016 | Slaughter et al. |
| 2015/0181781 | P1 | 6/2015 | Slaughter et al. |

*Primary Examiner* — Susan McCormick Ewoldt
(74) *Attorney, Agent, or Firm* — Potter Anderson & Corroon LLP

(57) ABSTRACT

A new and distinct variety of nectarine tree (*Prunus persica nucipersica*), which is denominated varietally as 'Wanectfive', and which produces an attractively colored white-fleshed, clingstone nectarines which is mature for harvesting and shipment approximately June 1 to June 10 under the ecological conditions prevailing in the San Joaquin Valley of central California.

2 Drawing Sheets

Botanical designation: '*Prunus persica nucipersica*'.
Varietal denomination: 'Wanectfive'.

BACKGROUND OF THE NEW VARIETY

The present variety of nectarine tree resulted from an on-going program of fruit and nut tree breeding. The purpose of this program is to improve the commercial quality of deciduous fruit varieties and rootstocks by creating and releasing promising selections of *Prunus* species. To this end, both controlled and hybrid cross pollinations are made each year to produce seedling populations from which improved progenies are evaluated and selected.

The seedling, 'Wanectfive' was originated by the breeders and selected from a population of seedlings growing in the experimental orchards located near Fowler, Calif. The seedlings, grown on their own roots, were derived from planting seed of the seedling, "Burnecttwentyeight" (U.S. Plant Pat. No. 26,610), a yellow-fleshed nectarine used as the female parent. The pollen parent of this seedling was from an un-named, non-patented, white-fleshed nectarine seedling. The resulting fruit was collected from the female parent at a mature stage, and seeds were extracted in June of 2013. After a period of stratification, the seed was placed in the greenhouse by population and then field planted for tree establishment, and ultimately to exhibit fruit for evaluation. One white-fleshed nectarine seedling, which is the present variety, exhibited especially desirable characteristics, and was then designated as 'V5.055.119'. This seedling was marked for subsequent observation. After the 2017 fruiting season, the new variety of nectarine tree was selected for advanced evaluation and repropagation.

ASEXUAL REPRODUCTION

Asexual reproduction of this new and distinct variety of nectarine tree was accomplished by budding the new nectarine tree onto 30 trees of 'Nemaguard' Rootstock (unpatented). This was performed by the breeders in an experimental orchard located near Fowler, Calif. Subsequent evaluations of these asexually reproduced plants have shown those asexual reproductions run true to the original tree. All characteristics of the original tree, and its fruit, were established and appear to be transmitted through these succeeding asexual propagations.

SUMMARY OF VARIETY

'Wanectfive' is a new and distinct variety of nectarine tree, which is considered of relatively large size, and which has a vigorous growth characteristic. This new tree is also a regular and productive bearer of relatively large, firm, white-fleshed, low acid fleshed clingstone fruit which have a very good flavor and eating qualities.

This new nectarine tree has a medium chilling requirement of approximately 400 hours, and further produces relatively uniformly sized fruit throughout the tree's canopy. In addition to the foregoing, the fruit of the new nectarine also appears to have good handling and shipping qualities. The 'Wanectfive' Nectarine tree bears fruit which are typically ripe for commercial harvesting and shipment on approximately June 1 to June 10 under the ecological conditions prevailing in the San Joaquin Valley of central California. In relative comparison to the 'Pearlicious III' nectarine tree (U.S. Plant Pat. No. 18,706), which is the closest known variety, the current variety of nectarine tree bears fruit that is clingstone and the comparator variety produces fruit that is freestone. In relative comparison to 'Burnecttwentyeight' (U.S. Plant Pat. No. 26,610) nectarine seed parent tree, the current variety is contrasted by ripening approximately 10 days earlier. Further, the current variety is white-fleshed, whereas the seed parent exhibits yellow flesh. In comparing the current variety to its un-named, unpatented nectarine pollen parent, the current variety is about 5 to about 7 millimeters (mm) larger and 5 days later.

Figure 1:
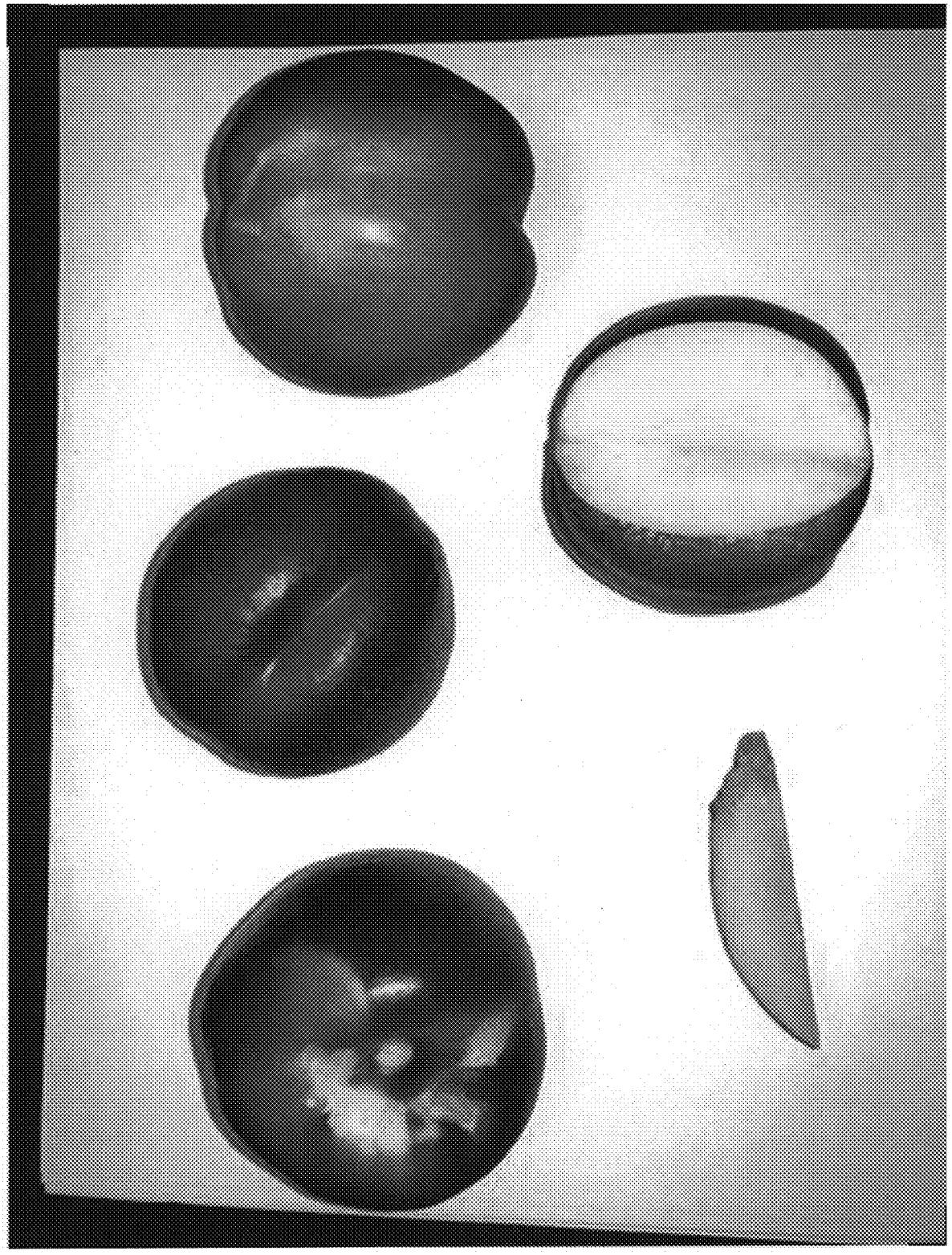
FIG. 1 is a color photograph of three whole mature fruit harvested from a fifth leaf year tree displaying the sutural (left, top), basal (left, middle), and apical (left, bottom) fruit aspects. One mature fruit is sliced through the sagittal plane (right), and which reveals the flesh color. The external coloration of the fruit is sufficiently matured for harvesting and shipment.
Figure 2:
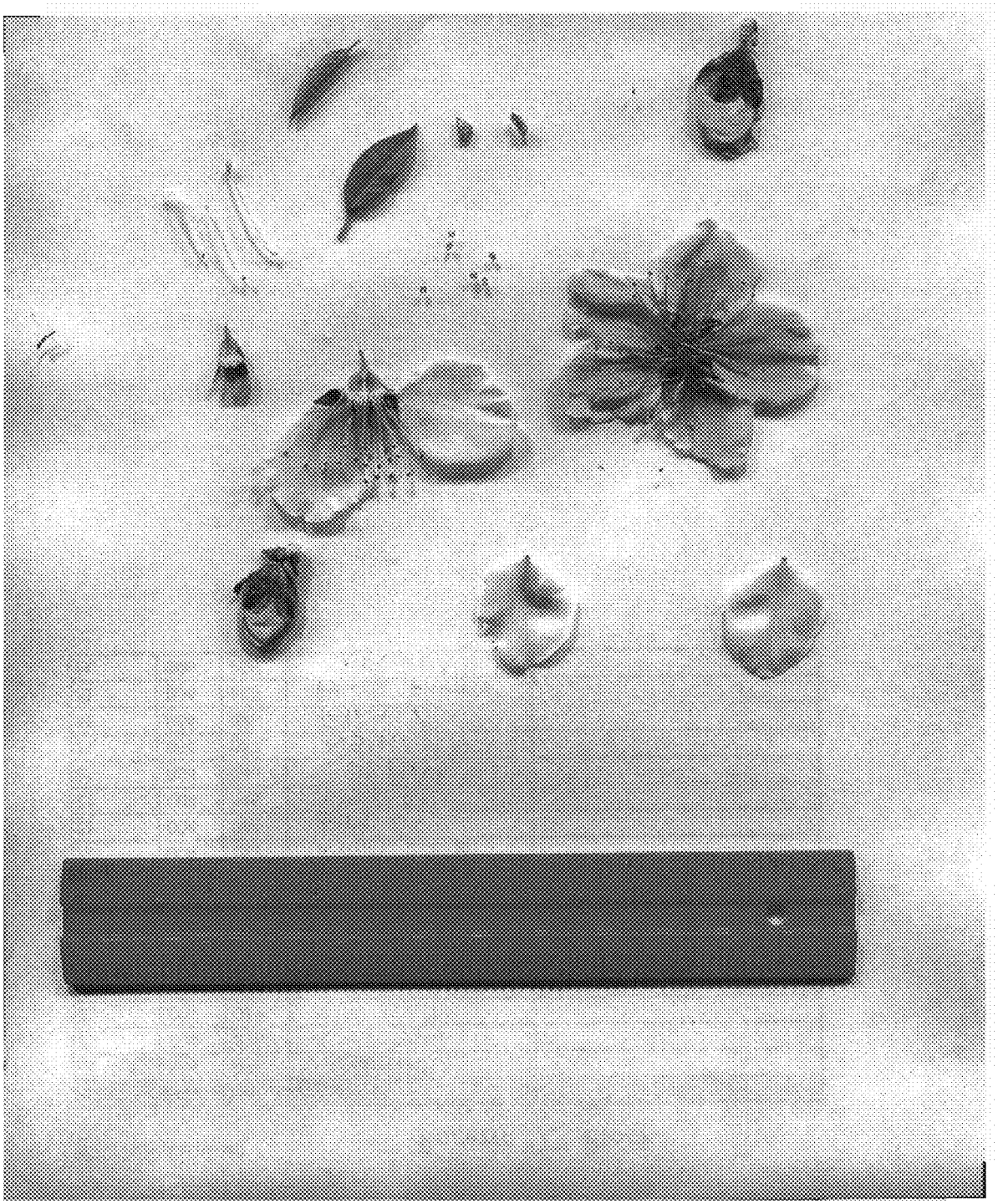
FIG. 2 is a color photograph displaying typical flower buds, flower petals, and flower blooms.

The colors in these photographs are as nearly true as is reasonably possible in a color representation of this type. Due to chemical development, processing and printing, the leaves and fruit depicted in these photographs may, or may not, be accurate when compared to the actual specimen. For this reason, future color references should be made to the color plates (Royal Horticultural Society, Fourth Edition, 2001) and descriptions provided, hereinafter.

NOT A COMMERCIAL WARRANTY

The following detailed description has been prepared to solely comply with the provisions of 35 U.S.C. § 112, and does not constitute a commercial warranty (either expressed or implied) that the present variety will in the future display all the botanical, pomological, or other characteristics as set forth hereinafter. Therefore, this disclosure may not be relied upon to support any future legal claims including, but not limited to, breach of warranty of merchantability, or fitness for any purpose, or non-infringement which is directed, in whole, or in part, to the present variety.

DETAILED DESCRIPTION

Referring more specifically to the pomological details of this new and distinct variety of nectarine tree, the following has been observed during the tenth fruiting season, and under the ecological conditions prevailing at orchards located near the town of Fowler, county of Fresno, state of California. All major color code designations are by reference to The R.H.S. Colour Chart (Royal Horticultural Society, Fourth Edition, 2001) provided by The Royal Horticultural Society of Great Britain. Common color names are also occasionally used.

TREE

Size: Generally considered medium-large in its growth pattern as compared to other common commercial nectarine cultivars ripening in the late season of maturity. The tree of the present variety was pruned to a height of about 270.0 cm to about 310.0 cm at commercial maturity. Tree size can vary with crop load and the conditions under which the fruit and tree are grown.

Width: About 265.0 cm.

Vigor: Considered moderately vigorous. The present nectarine tree variety grew from about 175.0 cm to about 180.0 cm in height during the first growing season. The new variety was pruned to a height of about 150.0 cm during the first dormant season, and primary scaffolds were then selected for the desired tree structure.

Productivity: Productive. Fruit set varies from more than the desired crop load to levels higher than desired amounts, when the new variety is grown in a suitable horticultural zone, and under appropriate commercial orchard conditions. The number of the fruit set varies with the prevailing climatic conditions, and the cultural practices employed. The fruit set is spaced by thinning to develop the remaining fruit into the desired market-sized fruit.

Fruit bearing: Regular. Fruit set has been more than adequate during the previous years of observation, and thinning was necessary during the past 7 years on both the original seedling and on subsequent asexually reproduced trees.

Tree form: Upright and pruned into a vase shape.

Density: Considered moderately dense.

Hardiness: The present tree was grown and evaluated in USDA Hardiness Zone 9. The calculated winter chilling requirements of the new tree is approximately 400 hours at a temperature below 7.0 degrees C.

The present variety appears to be hardy under typical central San Joaquin Valley climatic conditions.

TRUNK

Diameter: About 24.0 cm in diameter when measured at a distance of approximately 15.5 cm above the soil level. This measurement was taken at the beginning of the 8th growing season.

Bark texture: Considered moderately rough, with folds of papery scarfskin being present. Since bark development and coloration change with advancing tree age, this characteristic varies with the tree vigor, age, and regional conditions. Therefore, this is not a dependable descriptor of the new variety.

Lenticels: Numerous flat, oval lenticels are present. The lenticels range in size from about 2.0 mm to about 5.0 mm in width, and between about 1.5 mm and about 2.5 mm in height. The development and size of the trunk lenticels can be influenced, to some degree, by the ambient growing conditions, and are not necessarily a dependable characteristic of this variety. As trees of this variety mature, lenticels are present, but they are generally covered by increasing layers of cork (mature bark) and therefore become less apparent.

Lenticel color: Considered an orange brown (RHS Greyed-Orange Group 167 B).

Bark coloration: Variable, but it is generally considered to be a greyed green (RHS Greyed-Green Group 197 B). This bark description was taken from trees in their eighth leaf which have ruptured the scarf skin, and which also have developed bark furrowing which is much more typical of the bark of older trees.

BRANCHES

Size: Considered medium large for the variety.

Diameter: Average as compared to other nectarine varieties. The branches have a diameter of about 15.0 cm when measured during the 8th year after grafting.

Flowering shoot thickness: Average for the species. Generally, the most consistent flower bud development, and therefore potential fruiting sites, occur on shoots which are about 8.0 mm in diameter, or larger, but generally less than 16.0 mm in diameter at the time of bloom.

Surface texture: Average and appearing relatively smooth, but with more furrowing on wood which is several years old.

Crotch angles: Primary branches are considered variable and are usually growing at an angle of about 50 degrees when measured from a horizontal plane.

Current season shoots:

*Surface texture.*—Substantially glabrous.

Internode length: About 3.0 cm.

Color of mature branches: Approximately Grey brown (RHS Greyed-Orange Group 177 A).

Current season's shoots:

*Color.*—Light green (RHS Yellow-Green Group 145 B). The color of new shoot tips is considered a bright and shiny green (RHS Yellow-Green Group 146 D).

LEAVES

Size: Considered somewhat large for the species. Leaf measurements have been taken from vigorous, upright, current-season growth, at approximately mid-shoot. The leaf size is often influenced by prevailing growing conditions, quality and intensity of available sunlight, and the location of the leaf within the tree canopy. For this reason, leaves sizes can vary significantly based upon the ambient light and other cultural factors listed above and are not typically considered a dependable botanical descriptor.

Leaf arrangement: The leaves are arranged in a spiral pattern of 4:1 typical of *Prunus* genera.

Leaf length: About 170.0 mm to about 190.0 mm (including the petiole).

Leaf width: About 45.0 mm to about 50.0 mm.

Leaf base-shape: The leaves generally exhibit equal marginal symmetry relative to the leaf longitudinal axis.

Leaf form: Lanceolate.

Leaf tip form: Acuminate.

Leaf color:

*Upper leaf surface.*—Medium green (approximately RHS Green Group 137 B).

Leaf texture:

*Upper leaf surface.*—Glabrous.

*Lower leaf surface.*—Glabrous.

Leaf color:

*Lower leaf surface.*—Medium green (approximately RHS Green Group 137 C).

Leaf venation: Pinnately veined.

Mid-vein:

*Color.*—Considered a pale green (approximately RHS Yellow-Green Group 145 C).

Leaf margins: Gently undulating.

*Form.*—Considered crenulate.

*Uniformity.*—Generally uniform.

Leaf petioles:

*Form.*—Considered canaliculated and having a more pronounced trough when viewed from the dorsal aspect. The petiole margin is considered rounded when viewed from the ventral aspect.

*Size.*—Considered medium for the species.

*Length.*—About 6.0 mm to about 9.0 mm.

*Diameter.*—About 1.5 mm to about 2.0 mm.

*Color.*—A yellowed green (approximately RHS Yellow-Green Group 144 B).

*Texture.*—Glabrous.

*Strength.*—Durable for species until senescence.

Leaf glands:

*Size.*—Considered relatively small for the species; about 2.0 mm. in length; and about 0.5 mm to about 1.0 mm in width.

*Number.*—Generally, one and, less common, two glands appear per marginal side are found. Observations of more than two glands per marginal side are very uncommon.

*Type.*—Glands located at the base of the leaf are predominantly reniform in shape. An additional one to two, or occasionally more glands, which appear reniform, and stalked, gland primordia are often present at the basal margin of the leaf petiole as well.

*Color.*—(Approximately RHS Greyed-Brown Group N199 D). Typically, the coloration of the glands darkens, and occasionally begins to desiccate relatively early in the growing season.

Leaf stipules:

*Size.*—Medium large for this variety.

*Length.*—About 14.0 mm.

*Width.*—About 2.0 mm.

*Number.*—Typically, 2 per leaf bud, and up to 6 per shoot tip.

*Form.*—Lanceolate in form and having a strongly serrated marginal edge.

*Color.*—Green (approximately RHS Yellow-Green Group 141 B) when young, but graduating to a brown color (approximately RHS Greyed-Orange Group 165 A) with advancing senescence. The leaf stipules are generally considered to be early deciduous.

FLOWER BUDS

Hardiness: No winter injury (bud death) has been noted during the last several years of observation in the central San Joaquin Valley. The new variety of nectarine tree has not been intentionally subjected to drought, cold or heat stress, and therefore this information is not available.

Flower bud:

*Size.*—Variable, and dependent on the state of maturity. The flower buds as described were observed approximately 2 days into bloom.

*Length.*—About 19.5 mm.

*Diameter.*—About 11.0 mm.

*Surface texture.*—Pubescent.

*Orientation.*—Considered appressed, but appear less so as the blossoms near opening.

*Shape.*—Considered ovoid.

Bud scale color: Approximately RHS Greyed-Orange Group 175 A.

FLOWERS

Date of first bloom: Observed on Feb. 19, 2021.

*Blooming time.*—Considered average to slightly early mid-bloom in relative comparison to other commercial nectarine cultivars grown in the central San Joaquin Valley. The date of full bloom was observed on Feb. 25, 2021. The date of full bloom varies slightly with climatic conditions and prevailing cultural practices.

*Duration of bloom.*—Approximately 8 or more days. This characteristic varies slightly with the prevailing climatic conditions.

Flower class: Considered a perfect flower, complete and perigynous.
Flower type: The variety is considered to have a showy type flower.
Flower size: Considered very large. The flower diameter at full bloom is about 47.0 mm to about 51.0 mm.
Bloom quantity: Considered abundant.
Flower bud density: Generally considered dense.
*Flower bud frequency.*—Generally, two flower buds appear per node, but occasionally one flower bud per node is observed. Very rarely three floral buds per node are observed.
Petal size: Generally considered large for the species.
*Petal length.*—About 20.0 mm to about 23.0 mm.
*Petal width.*—About 16.0 mm to about 18.0 mm.
Petal form: Considered broadly ovate.
Petal count: Nearly always 5.
Petal texture:
*Upper petal texture.*—Very finely pubescent, satin like.
*Lower petal texture.*—Very finely pubescent, satin like.
Petal color: Both the upper and lower surfaces of the flower petal are considered a light pink at the popcorn stage (RHS Red Group 56 C).
Fragrance: Slight.
Petal claw:
*Form.*—The claw is considered ovate and is generally large.
*Length.*—About 13.0 mm.
*Width.*—About 11.0 mm.
Petal margins: Generally, slightly undulate.
Petal apex: Entire.
Flower pedicel:
*Length.*—Considered medium with an approximate length of about 1.5 mm to about 2.5 mm.
*Diameter.*—About 0.5 mm to about 1.0 mm.
*Color.*—A pale yellow-green (approximately RHS Yellow-Green Group 151 B), depending on pedicel and fruit maturity and timing of visual observance.
*Strength.*—Tenacious. Average for the species.
*Texture.*—Generally smooth to slightly undulate.
Floral nectaries:
*Color.*—Considered a pale yellow (approximately RHS Yellow-Orange Group 15 D).
Calyx:
*Surface texture.*—Finely pubescent.
*Color.*—Approximately RHS Greyed-Purple Group 185 A.
Sepals:
*Upper surface texture.*—Moderately pubescent.
*Lower surface texture.*—Glabrous.
*Number.*—5 sepals.
*Size.*—Considered medium.
*Sepal length.*—About 4.0 mm to about 6.0 mm.
*Sepal width.*—About 3.5 mm to about 5.0 mm.
*Sepal shape.*—Generally obovate.
*Sepal margin.*—Considered smooth and entire.
*Sepal color.*—Approximately RHS Greyed-Red Group 178 A.
Anthers:
*Generally.*—Average in size.
*Color.*—Yellow when viewed dorsally and prior to dehiscence (approximately RHS Yellow-Orange Group 22 A).
*Position relative to stigma.*—Generally, the stigma is superior to the anthers by about 1.0 mm to about 2.0 mm.
Pollen production: Pollen is abundant and has a yellow color (approximately RHS Yellow-Orange Group 22 A).
Fertility: Self-fertile.
Filaments:
*Size.*—About 13.5 mm to about 16.0 mm in length.
*Color.*—Considered a pale pink (RHS Red Group 56 C).
Pistil:
*Number.*—Usually one, and only rarely more than one.
*Generally.*—Considered medium-large in size.
*Length.*—About 19.0 mm to about 21.0 mm in length including the ovary.
*Diameter.*—About 0.5 mm to about 1.0 mm.
*Color.*—Considered a very pale green (approximately RHS Yellow-Green Group 150 D).
*Surface texture.*—The variety has a long glabrous pistil.
*Position relative to petals.*—At flower maturity the stamens grow to be superior to the petals.
*Ovary surface texture.*—Glabrous.

FRUIT

Maturity when described: Firm ripe condition (shipping ripe).
Date of first picking: Approximately Jun. 3, 2021.
Date of last picking: Jun. 13, 2021. The date of harvest can vary with the prevailing climatic conditions, crop loads, and the current climatic and cultural practices.
Size:
*Generally.*—Considered large.
Average cheek diameter: About 80.0 mm to about 84.0 mm.
Average axial diameter: About 74.0 mm to about 79.0 mm.
Typical weight: About 277.0 grams. The fruit size and weight can vary and are dependent on the prevailing cultural practices and growing conditions, and therefore is not particularly distinctive of the new variety.
Fruit soluble solids: Approximately 15.5 to 18.0 Brix. Fruit sugar levels can vary significantly depending on fruit maturity, local and seasonal climatic conditions, and fruit per tree.
Fruit firmness: Fruit flesh pressures generally averaged about 13.0 pounds at the time the fruit was analyzed.
Titratable acidity: Approximately 0.28 to 0.35 at commercial harvest maturity.
Fruit form:
*Generally.*—Considered globose to slightly oblate. The fruit is generally very uniform in symmetry.
Mucron tip: Absent.
Fruit suture: No stitching exists along the suture line.
Suture:
*Color.*—Generally, the fruit appears blushed to the same degree as the skin (approximately RHS Red-Purple Group 59 A).
Ventral surface:
*Form.*—Considered even and uniform in appearance when it is viewed from the lateral, sutural plane.
Apex:
*Shape.*—Slightly retuse.
Base:
*Shape.*—Generally smooth.

Stem cavity:

*Generally.*—It extends in a rounded circular form, which is generally considered uniform. The stem cavity is rounded but extended toward the suture. The average depth of the stem cavity is about 10.0 mm to about 13.0 mm. The average width of the stem cavity is about 17.5 mm. The average length of the stem cavity, when measured in the suturial plane, is about 29.0 mm.

Fruit skin:

*Thickness.*—Considered medium in thickness, and tenacious to the flesh.

*Surface texture.*—Glaborous.

*Conspicuousness of lenticels.*—Occasionally present, most noted laterally and toward the apex of the fruit.

*Taste.*—Non-astringent.

*Tendency to crack.*—Not observed in the previous years of observation and evaluation.

Fruit skin color:

*Blush color.*—Generally speaking, a red blush exists on a majority of the skin of the fruit (approximately RHS Red-Purple Group 59 A), and is more typically present on the portions of the fruit facing the sunlight. The blush of the fruit typically covers approximately 85% to 95% of the fruit skin surface. The percentage of the blush on the fruit skin surface can vary, and is generally dependent upon the fruit's exposure to direct sunlight; specific fruit maturity; and also, the prevailing ecological and cultural conditions under which the fruit was grown.

Ground color: A faint yellowish white (approximately RHS White Group 155 B). The ground color of the fruit can vary significantly based upon the maturity of the fruit when this measurement is taken, and generally gains a lighter and less green cast with higher maturity.

Fruit glossiness: Fruit is considered to be medium in glossiness.

Fruit stem:

*Size.*—Medium in length, about 6.0 mm to about 8.0 mm.

*Diameter.*—About 3.5 mm to about 4.5 mm.

*Color.*—Pale yellow-green (approximately RHS Yellow-Green Group N144 D).

Fruit flesh:

*Ripening.*—Considered even.

*Texture.*—Firm, crunchy, juicy, and dense. Considered non-melting in flesh classification.

*Fibers.*—Present, but not prominent.

*Aroma.*—Slight.

*Eating quality.*—Considered very good.

*Flavor.*—Considered sweet with medium-low acidity.

*Juice production.*—Moderate.

*Brix.*—About 15.0 to about 20.0 degrees. This characteristic varies slightly with the number of fruits per tree; fruit position on the tree; the maturity of fruit when harvested; the prevailing cultural practices; and the ambient climatic conditions.

*Acidity.*—Considered medium. Approximately 0.35 titratable acidity at fruit harvest.

*Flesh color.*—It is considered white (approximately RHS Yellow-White Group 158 B).

STONE

Type: Considered a clingstone.

Size: It is generally considered to be medium for the species.

Length: Average, about 33.0 mm to about 37.0 mm.

Width: Average, about 26.0 mm to about 30.0 mm.

Diameter: Average, about 18.0 mm to about 22.0 mm.

Form: Roughly ovoid.

Stone base:

*Shape.*—The stone is considered shortly attenuate.

Apex:

*Shape.*—The stone exhibits a slightly blunted apex.

Stone surface:

*Surface texture.*—Considered irregularly furrowed toward the apex. Further, more pitting exists in the mid-portion of the stone (laterally), and is more common toward the base.

*Ridges.*—Ridging is generally more prominent, and is usually oriented parallel, and laterally relative at the ventral and dorsal margins.

*Ventral edge.*—The ventral edge is generally described as having adjoining ridges formed from each hemisphere. There are longitudinal grooves running alongside this joined ventral suture. Secondarily, there can exist an additional set of parallel ridges, one on each side of the major ridge. These secondary ridges are less prominent and do not always extend from the hilum to the apex.

*Dorsal edge.*—Shape — Generally considered pronounced but even. The folds of the surface ridges appearing on the external margins often end gently along the suture.

Stone color: The color of a mature, dry stone is generally considered a dull brown (approximately RHS Greyed-Orange Group 166 B). Stone color can vary considering how recently the fruit has ripened, harvested, degree of oxidation, surface drying, and blanching due to exposure sunlight.

Tendency to split: Splitting has rarely been noted.

Kernel:

*Length.*—About 17.0 mm to about 21.0 mm.

*Width.*—About 15.0 mm to about 18.0 mm.

*Thickness.*—About 4.0 mm to about 6.0 mm.

*Size.*—The kernel is considered medium in size.

*Form.*—Considered generally ovoid.

*Kernel surface texture.*—Kernel pellicle is shortly pubescent.

*Color.*—A dark tan (RHS Greyed-Orange Group N163 C).

Use: The present variety 'Wanectfive' is considered to be a nectarine tree of the early season of maturity, and which produces fruit which are considered to be firm, attractively colored, and which are useful for both local and long distance shipping.

Keeping quality: Appears very good. The fruit of the present variety has stored well for periods of up to 21 days after harvest at 1.0 degree Celsius.

Shipping quality: Good. The fruit of the new nectarine tree variety showed minimal bruising of the flesh or skin damage after being subjected to normal harvesting and packing procedures.

Resistance to insects and disease: No susceptibilities were noted. The present variety has not been intentionally tested to expose or detect any susceptibilities or resistances to any known plant, fruit diseases, insect, frost, winter injury, or other environmental factors.

Although the new variety of nectarine tree possesses the described characteristics when grown under the ecological conditions prevailing near Fowler, Calif., in the Central part of the San Joaquin Valley of California, variations of the usual magnitude, and characteristics incident to changes in growing conditions, fertilization, nutrition, pruning, pest control, frost, climatic variables, and changes in horticultural management are to be expected.

Having thus described and illustrated our new variety of nectarine tree, what we claim is new, and desire to secure by plant Letters Patent is:

1. A new distinct variety of nectarine tree substantially as illustrated and described, and which is characterized principally as to novelty by producing an attractively colored white-fleshed, clingstone nectarine which is mature for harvesting and shipment approximately June 1 to June 10 under the ecological conditions prevailing in the San Joaquin Valley of central California.

* * * * *